(12) United States Patent
Xu

(10) Patent No.: US 12,128,093 B2
(45) Date of Patent: Oct. 29, 2024

(54) METHODS OF TREATING POLYCYSTIC KIDNEY DISEASE

(71) Applicant: Kai Yuan Xu, Cockeysville, MD (US)

(72) Inventor: Kai Yuan Xu, Cockeysville, MD (US)

( * ) Notice: Subject to any disclaimer, the term of this patent is extended or adjusted under 35 U.S.C. 154(b) by 428 days.

(21) Appl. No.: 17/234,726

(22) Filed: Apr. 19, 2021

(65) Prior Publication Data
US 2021/0299235 A1 Sep. 30, 2021

Related U.S. Application Data

(60) Provisional application No. 62/978,518, filed on Feb. 19, 2020.

(51) Int. Cl.
*C07K 16/40* (2006.01)
*A61K 39/00* (2006.01)
*A61P 13/12* (2006.01)

(52) U.S. Cl.
CPC .......... *A61K 39/0005* (2013.01); *A61P 13/12* (2018.01); *C07K 16/40* (2013.01); *A61K 2039/58* (2013.01); *C07K 2317/76* (2013.01)

(58) Field of Classification Search
None
See application file for complete search history.

(56) References Cited

U.S. PATENT DOCUMENTS

| | | | | |
|---|---|---|---|---|
| 7,728,114 B2 * | 6/2010 | Mach | ........................ | A61P 1/04 530/388.22 |
| 9,409,949 B2 | 8/2016 | Xu | | |
| 9,416,159 B2 | 8/2016 | Xu | | |
| 10,287,361 B2 | 5/2019 | Xu | | |
| 11,279,772 B2 | 3/2022 | Xu | | |
| 11,492,416 B2 | 11/2022 | Xu | | |

OTHER PUBLICATIONS

Harlow et al. (Antibodies, A Laboratory Manual, Cold Spring Harbor laboratory, 1988, pp. 37-47). (Year: 1988).*
Edwards et al. (J. Mol. Biol. (2003) 334, 103-118). (Year: 2003).*
Lloyd et al., Protein Engineering, Design & Selection vol. 22 No. 3 pp. 159-168, 2009). (Year: 2009).*
Meyer et al. (British Journal of Haematology, 2018, 180, 808-820, Supp Figs S1-S4 and pp. 1-5). (Year: 2018).*
Vajdos et al. (J Mol Biol. Jul. 5, 2002;320(2):415-28). (Year: 2002).*
Bedouelle et al. (FEBS J. Jan. 2006;273(1):34-46). (Year: 2006).*
Brown et al. (J Immunol. May 1, 1996;156(9):3285-91). (Year: 1996).*
Colman (Research in Immunology, 145:33-36, 1994). (Year: 1994).*
Rudikoff et al. (Proc. Natl. Acad. Sci. USA, 79: 1979-1983, Mar. 1982). (Year: 1982).*
Van Oss CJ, et al., Nature of the antigen-antibody interaction, Journal of Chromatography (1986) 376: 111-119.
Absolom DR, et al., The nature of the antigen-antibody bond and the factors . . . , CRC Critical Reviews in Immunology (1986) 6(1): 1-46.
Braden BC, et al., Protein motion and lock and key complementarity in antigen-antibody reactions, Pharm Acta Helv (1995) 69(4): 225-230.
Estep P, et al., High throughput solution-based measurement of antibody-antigen affinity and epitope binning, mAbs (2013) 5(2): 270-278.
Vauquelin G, et al., Exploring avidity: understanding the potential gains in functional affinity . . . , Br J Pharmacol (2013) 168:1771-1785.
Erlendsson S, et al., "Binding Revisited-Avidity in Cellular Function and Signaling". Front Mol Biosci (2020)7: 615565.
Sela-Culang I, et al., The structural basis of antibody-antigen recognition, Frontiers in Immunology. (2013) 4: 302.
Lee DI et al., Activation of (NaK)-ATPase Modulates Cardiac L-Type Ca2 Channel Function, Mol Pharmacol (2009)75:774-781.
Xu KY, et al., Serine496 of b2 subunit of L-type Ca2+ channel participates in molecular crosstalk between activation of (NaK)-ATPase . . . ,BBRC (2010)402:319-323.
Xu KY, et al., Mechanistic distinction between activation and inhibition of (Na++K+)-ATPase-mediated Ca2+ influx . . . , BBRC (2011)406:200-203.
Xu KY, Activation of (Na+K)-ATPase (as Breakthroughs), Biochem Biophys Res Commun (2005)338:1669-1677.
Trier N., et al., Peptides, Antibodies, Peptide Antibodies and More, Int J Mol Sci (2019)20:6289-6310.
Houen G, Peptide Antibodies: Past, Present, and Future, Methods Mol Biol (2015)1348:1-6.
Lee BS, et al., Production of antipeptide antibodies, Methods Mol Bio (2010)657:93-108.
Janeway C, Immunobiology (5th ed.), (2001), Garland Publishing, ISBN 978-0-8153-3642-6.
Goldberg RJ, (1952). A Theory of Antibody-Antigen Reactions, J Am Chem Soc (1952)74:5715-5725.
Sahimi, M, (1994). Applications of Percolation Theory. London: CRC Press. p. 257.
Spiers, JA, Goldberg's theory of antigen-antibody reactions in vitro, Immunology (1958)1(2): 89-102.
Janeway CA Jr, et al., (2001) Immunobiology: The Immune System in Health and Disease (5 ed.). New York: Garland Science.
Mian IS, et al., Structure, function and properties of antibody binding sites. Journal of Molecular Biology. (1991)217 (1): 133-151.

* cited by examiner

*Primary Examiner* — Zachary S Skelding

(57) ABSTRACT

Methods of preventing and treating PKD and its complications using antibody activators that bind to the (Na$^+$+K$^+$)-ATPase.

8 Claims, 6 Drawing Sheets

Specification includes a Sequence Listing.

Fig. 2
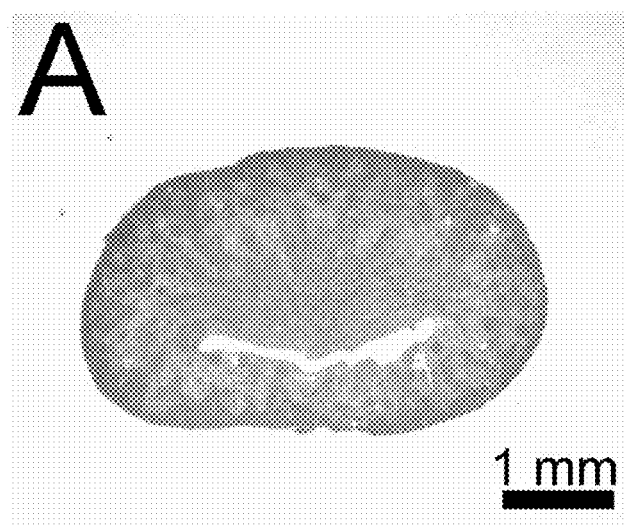
Fig. 2A
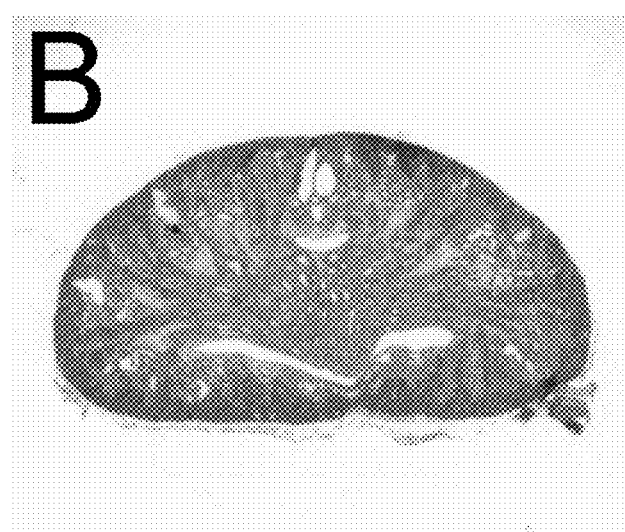
Fig. 2B
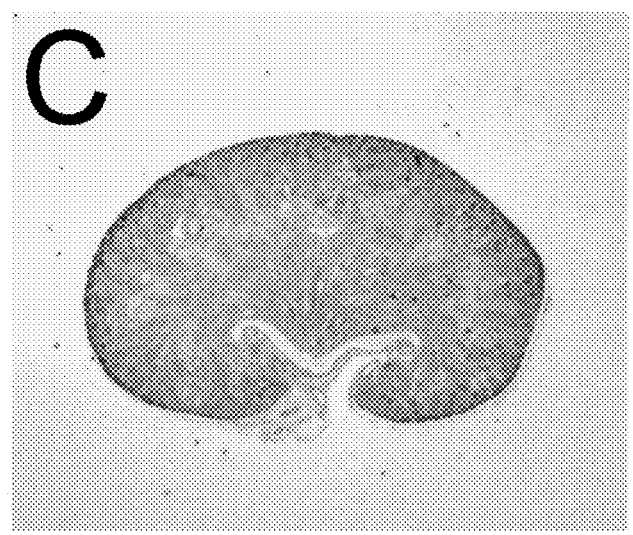
Fig. 2C

Fig. 3
Fig. 3A
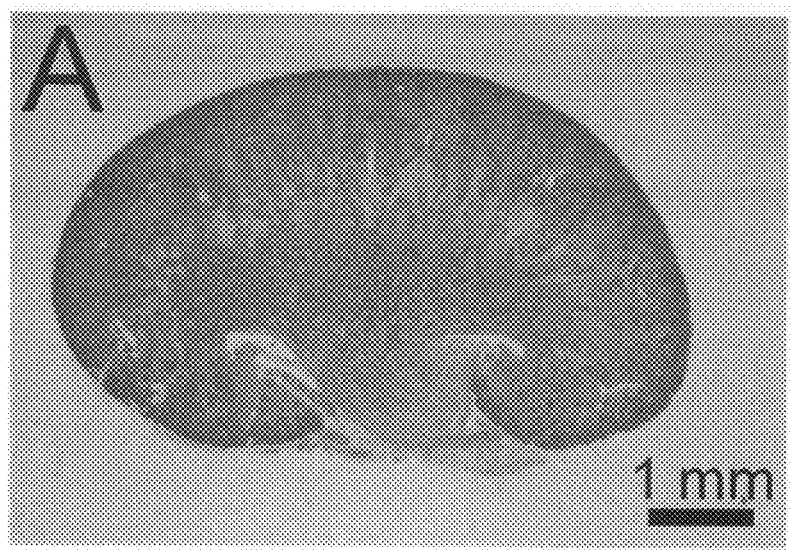
Fig. 3B
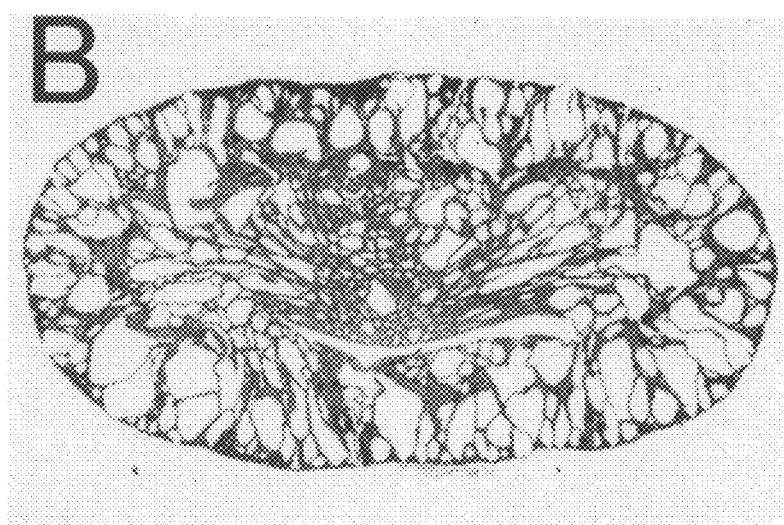
Fig. 3C
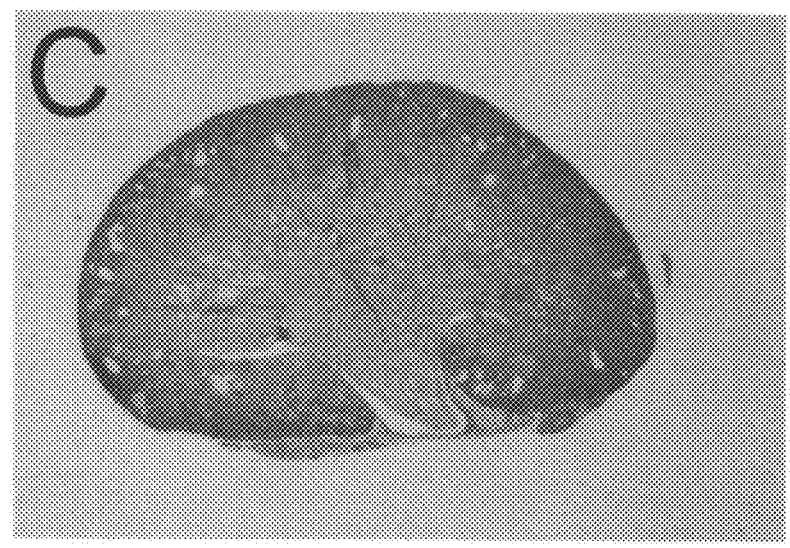

Fig. 6
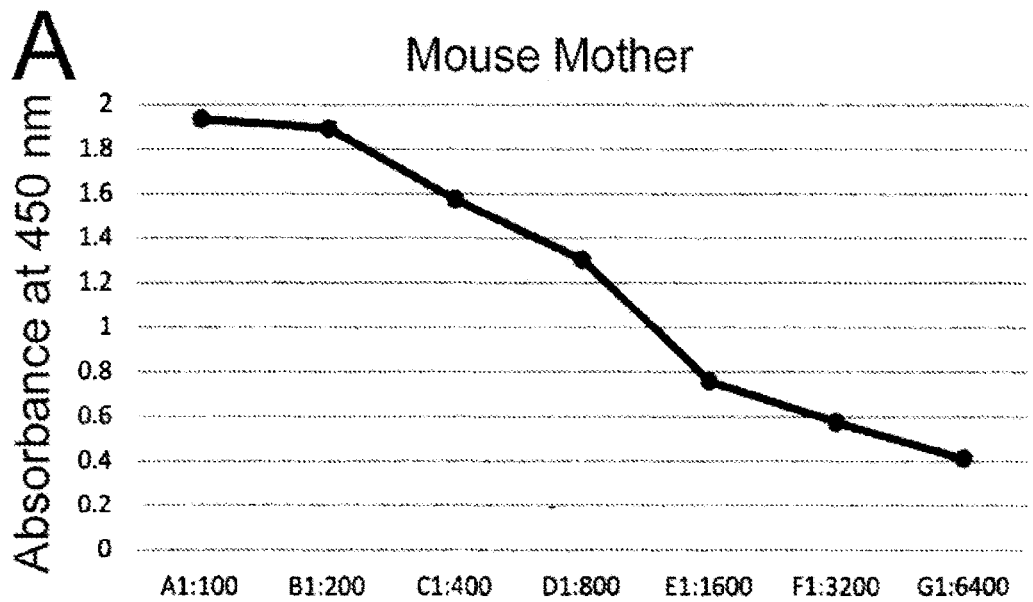
Fig. 6A
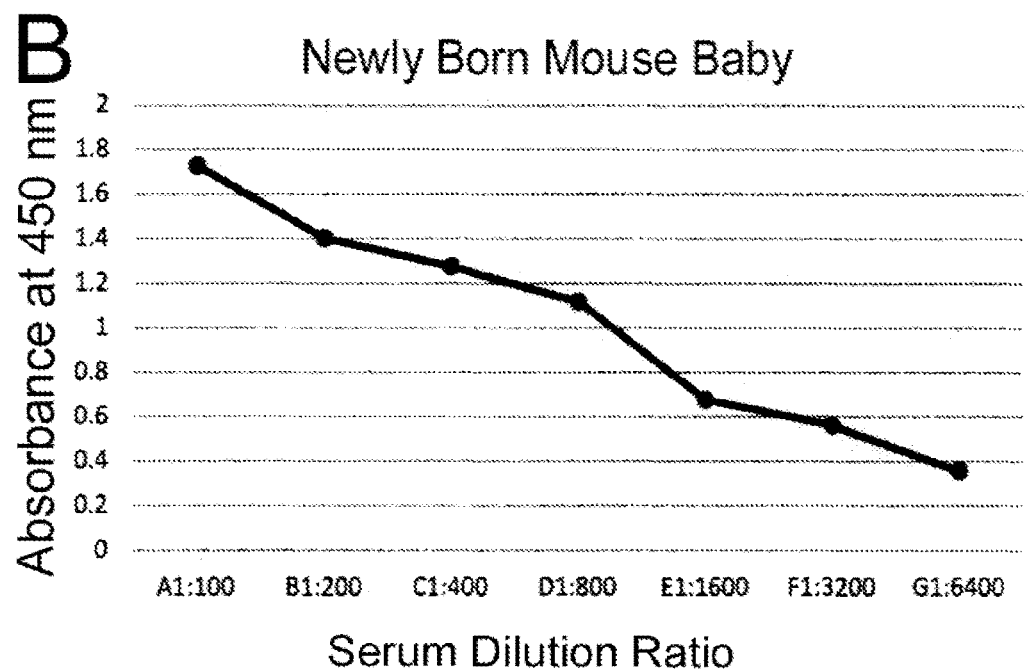
Fig. 6B
Serum Dilution Ratio

SEQUENCE LISTING

<160> NUMBER OF SEQ ID NOS: 17

<210> SEQ ID NO 1
<211> LENGTH: 15
<212> TYPE: PRT
<213> ORGANISM: Artificial Sequence
<220> FEATURE:
<223> OTHER INFORMATION: Activation site of the (Na+K)-ATPase

<400> SEQUENCE: 1

Lys Arg Gln Pro Arg Asn Pro Lys Thr Asp Lys Leu Val Asn Glu
1               5                   10                  15

<210> SEQ ID NO 2
<211> LENGTH: 13
<212> TYPE: PRT
<213> ORGANISM: Artificial Sequence
<220> FEATURE:
<223> OTHER INFORMATION: Activation site of the (NA+K)-ATPase

<400> SEQUENCE: 2

Val Pro Ala Ser Leu Ala Tyr Glu Gln Ala Glu Ser Asp
1               5                   10

<210> SEQ ID NO 3
<211> LENGTH: 12
<212> TYPE: PRT
<213> ORGANISM: Artificial Sequence
<220> FEATURE:
<223> OTHER INFORMATION: Activation site of the (Na+K)-ATPase

<400> SEQUENCE: 3

Arg Ser Ala Thr Glu Glu Glu Pro Pro Asn Asp Asp
1               5                   10

<210> SEQ ID NO 4
<211> LENGTH: 15
<212> TYPE: PRT
<213> ORGANISM: Artificial Sequence
<220> FEATURE:
<223> OTHER INFORMATION: Activation site of the (Na+K)-ATPase

<400> SEQUENCE: 4

His Leu Leu Gly Ile Arg Glu Thr Trp Asp Asp Arg Trp Ile Asn
1               5                   10                  15

<210> SEQ ID NO 5
<211> LENGTH: 15
<212> TYPE: PRT
<213> ORGANISM: Artificial Sequence
<220> FEATURE:
<223> OTHER INFORMATION: Activation site of the (Na+K)-ATPase

<400> SEQUENCE: 5

Asp Val Glu Asp Ser Tyr Gly Gln Gln Trp Thr Tyr Glu Gln Arg
1               5                   10                  15

<210> SEQ ID NO 6
<211> LENGTH: 13
<212> TYPE: PRT
<213> ORGANISM: Artificial Sequence
<220> FEATURE:
<223> OTHER INFORMATION: Activation site of the (Na+K)-ATPase

<400> SEQUENCE: 6

Lys Glu Arg Gly Glu Phe Asn His Glu Arg Gly Glu Arg
1               5                   10

<210> SEQ ID NO 7
<211> LENGTH: 13
<212> TYPE: PRT
<213> ORGANISM: Artificial Sequence
<220> FEATURE:
<223> OTHER INFORMATION: Activation site of the (Na+K)-ATPase

<400> SEQUENCE: 7

Arg Asp Glu Asp Lys Asp Lys Val Gly Asn Ile Glu Tyr
1               5                   10

<210> SEQ ID NO 8
<211> LENGTH: 122
<212> TYPE: PRT
<213> ORGANISM: Artificial Sequence
<220> FEATURE:
<223> OTHER INFORMATION: Mouse monoclonal antibody

<400> SEQUENCE: 8

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Ser Tyr
            20                  25                  30

Trp Met His Val Lys Gln Arg Pro Gly Gln Gly Leu Glu Trp Ile
        35                  40                  45

Gly Thr Ile Asn Pro His Ser Gly Ser Tyr Tyr Ser Glu Lys Phe
    50                  55                  60

Lys Ser Lys Ala Thr Leu Thr Ala Asp Thr Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Thr Ala Val Ala Gly Gly Tyr Tyr Asp Gln Gly Ala Leu Asp Tyr Trp
            100                 105                 110

Gly Arg Gly Thr Ser Val Thr Val Ser Ser
        115                 120

<210> SEQ ID NO 9
<211> LENGTH: 112
<212> TYPE: PRT
<213> ORGANISM: Artificial Sequence
<220> FEATURE:
<223> OTHER INFORMATION: Mouse monoclonal antibody

<400> SEQUENCE: 9

Asp Ile Val Met Ser Gln Ser Pro Ser Ser Leu Ala Val Ser Ala Gly
1               5                   10                  15

Glu Lys Val Thr Met Ser Cys Lys Ser Ser Gln Ser Leu Phe Asn Ser
            20                  25                  30

Arg Thr Arg Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Lys Gln
                85                  90                  95

Tyr Ser Tyr Leu Arg Thr Phe Gly Gly Gly Thr Lys Leu Glu Ile Lys
            100                 105                 110

```
<210> SEQ ID NO 10
<211> LENGTH: 122
<212> TYPE: PRT
<213> ORGANISM: Artificial Sequence
<220> FEATURE:
<223> OTHER INFORMATION: Mouse monoclonal antibody

<400> SEQUENCE: 10

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Ser Tyr
                20                  25                  30

Trp Met His Trp Val Lys Gln Arg Pro Gly Gln Gly Leu Glu Trp Ile
            35                  40                  45

Gly Thr Ile Asn Pro His Ser Gly Ser Ser Tyr Tyr Ser Glu Lys Phe
        50                  55                  60

Lys Ser Lys Ala Thr Leu Thr Ala Asp Thr Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Thr Ala Val Ala Gly Gly Tyr Tyr Asp Gln Gly Ala Leu Asp Tyr Trp
            100                 105                 110

Gly Arg Gly Thr Ser Val Thr Val Ser Ser
        115                 120

<210> SEQ ID NO 11
<211> LENGTH: 112
<212> TYPE: PRT
<213> ORGANISM: Artificial Sequence
<220> FEATURE:
<223> OTHER INFORMATION: Mouse monoclonal antibody

<400> SEQUENCE: 11

Asp Ile Val Met Ser Gln Ser Pro Ser Ser Leu Ala Val Ser Ala Gly
1               5                   10                  15

Glu Lys Val Thr Met Ser Cys Lys Ser Ser Gln Ser Leu Phe Asn Ser
                20                  25                  30

Arg Thr Arg Lys Asn Tyr Leu Ala Trp Tyr Gln Gln Lys Pro Gly Gln
            35                  40                  45

Ser Pro Lys Leu Leu Ile Tyr Trp Ala Ser Thr Arg Glu Ser Gly Val
        50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Lys Gln
                85                  90                  95

Tyr Ser Tyr Leu Arg Thr Phe Gly Gly Gly Thr Lys Leu Glu Ile Lys
            100                 105                 110

<210> SEQ ID NO 12
<211> LENGTH: 122
<212> TYPE: PRT
<213> ORGANISM: Artificial Sequence
<220> FEATURE:
<223> OTHER INFORMATION: Mouse monoclonal antibody

<400> SEQUENCE: 12

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Ser Tyr
```

```
              20                  25                  30

Trp Met His Trp Val Lys Gln Arg Pro Gly Gln Gly Leu Glu Trp Ile
             35                  40                  45

Gly Thr Ile Asn Pro His Ser Gly Ser Ser Tyr Tyr Ser Glu Lys Phe
         50                  55                  60

Lys Ser Lys Ala Thr Leu Thr Ala Asp Thr Ser Ser Ser Thr Ala Tyr
 65                  70                  75                  80

Met Gln Leu Ser Ser Leu Thr Ser Glu Asp Ser Ala Val Tyr Tyr Cys
                 85                  90                  95

Thr Ala Val Ala Gly Gly Tyr Tyr Asp Gln Gly Ala Leu Asp Tyr Trp
                100                 105                 110

Gly Arg Gly Thr Ser Val Thr Val Ser Ser
                115                 120

<210> SEQ ID NO 13
<211> LENGTH: 112
<212> TYPE: PRT
<213> ORGANISM: Artificial Sequence
<220> FEATURE:
<223> OTHER INFORMATION: mouse monoclonal antibody

<400> SEQUENCE: 13

Asp Ile Val Met Ser Gln Ser Pro Ser Ser Leu Ala Val Ser Ala Gly
 1               5                  10                  15

Glu Lys Val Thr Met Ser Cys Lys Ser Ser Gln Ser Leu Phe Asn Ser
             20                  25                  30

Arg Thr Arg Lys Asn Tyr Leu Ala Trp Tyr Gln Gln Lys Pro Gly Gln
         35                  40                  45

Ser Pro Lys Leu Leu Ile Tyr Trp Ala Ser Thr Arg Glu Ser Gly Val
     50                  55                  60

Pro Asp Arg Phe Thr Gly Ser Gly Ser Gly Thr Asp Phe Thr Leu Thr
 65                  70                  75                  80

Ile Ser Ser Val Gln Ala Glu Asp Leu Ala Val Tyr Tyr Cys Lys Gln
                 85                  90                  95

Tyr Ser Tyr Leu Arg Thr Phe Gly Gly Gly Thr Lys Leu Glu Ile Lys
                100                 105                 110

<210> SEQ ID NO 14
<211> LENGTH: 122
<212> TYPE: PRT
<213> ORGANISM: Artificial Sequence
<220> FEATURE:
<223> OTHER INFORMATION: mouse monoclonal antibody

<400> SEQUENCE: 14

Gln Val Gln Leu Gln Gln Pro Gly Ala Glu Leu Val Lys Pro Gly Ala
 1               5                  10                  15

Ser Val Lys Leu Ser Cys Lys Ala Ser Gly Tyr Thr Phe Thr Ser Tyr
             20                  25                  30

Trp Met His Trp Val Lys Gln Arg Pro Gly Gln Gly Leu Glu Trp Ile
             35                  40                  45

Gly Thr Ile Asn Pro His Ser Gly Ser Ser Tyr Tyr Ser Glu Lys Phe
         50                  55                  60

Lys Ser Lys Ala Thr Leu Thr Ala Asp Thr Ser Ser Ser Thr Ala Tyr
 65                  70                  75                  80

Met Gln Leu Ser Ser Leu Thr Ser Glu Asp Ser Ala Val Tyr Tyr Cys
                 85                  90                  95
```

Thr Ala Val Ala Gly Gly Tyr Tyr Asp Gln Gly Ala Leu Asp Tyr Trp
            100                 105                 110

Gly Arg Gly Thr Ser Val Thr Val Ser Ser
        115                 120

<210> SEQ ID NO 15
<211> LENGTH: 112
<212> TYPE: PRT
<213> ORGANISM: Artificial Sequence
<220> FEATURE:
<223> OTHER INFORMATION: mouse monoclonal antibody

<400> SEQUENCE: 15

Asp Ile Val Met Ser Gln Ser Pro Ser Ser Leu Ala Val Ser Ala Gly
1               5                   10                  15

Glu Lys Val Thr Met Ser Cys Lys Ser Gln Ser Leu Phe Asn Ser
            20                  25                  30

Arg Thr Arg Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Lys Gln
                85                  90                  95

Tyr Ser Tyr Leu Arg Thr Phe Gly Gly Gly Thr Lys Leu Glu Ile Lys
            100                 105                 110

<210> SEQ ID NO 16
<211> LENGTH: 122
<212> TYPE: PRT
<213> ORGANISM: Artificial Sequence
<220> FEATURE:
<223> OTHER INFORMATION: mouse monoclonal antibody

<400> SEQUENCE: 16

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Thr Ile Asn Pro His Ser Gly Ser Ser Tyr Ser Glu Lys Phe
    50                  55                  60

Lys Ser Lys Ala Thr Leu Thr Ala Asp Thr Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Thr Ala Val Ala Gly Gly Tyr Tyr Asp Gln Gly Ala Leu Asp Tyr Trp
            100                 105                 110

Gly Arg Gly Thr Ser Val Thr Val Ser Ser
        115                 120

<210> SEQ ID NO 17
<211> LENGTH: 112
<212> TYPE: PRT
<213> ORGANISM: Artificial Sequence
<220> FEATURE:
<223> OTHER INFORMATION: mouse monoclonal antibody

```
<400> SEQUENCE: 17

Asp Ile Val Met Ser Gln Ser Pro Ser Ser Leu Ala Val Ser Ala Gly
1               5                   10                  15

Glu Lys Val Thr Met Ser Cys Lys Ser Ser Gln Ser Leu Phe Asn Ser
                20                  25                  30

Arg Thr Arg Lys Asn Tyr Leu Ala Trp Tyr Gln Gln Lys Pro Gly Gln
            35                  40                  45

Ser Pro Lys Leu Leu Ile Tyr Trp Ala Ser Thr Arg Glu Ser Gly Val
        50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Lys Gln
                85                  90                  95

Tyr Ser Tyr Leu Arg Thr Phe Gly Gly Gly Thr Lys Leu Glu Ile Lys
                100                 105                 110
```

METHODS OF TREATING POLYCYSTIC KIDNEY DISEASE

TECHNICAL FIELD

The invention relates to methods for preventing/treating autosomal dominant polycystic kidney disease (ADPKD or PKD) and its complications using peptide vaccine and antibodies (including both endogenous and exogenous) that bind to alpha (α) subunit or beta (β) subunit, or both, of the (Na⁺+K⁺)-ATPase (NKA) and increase NKA activity. Antibody capable of increasing NKA activity (activation of NKA) is called NKA agonist or NKA activator antibody. In addition, PKD and its complications can also be prevented and treated by administration of an antigenic NKA α or β subunits peptides that induce the production of endogenous antibodies, which specifically bind to the α or β subunits of NKA.

BACKGROUND OF INVENTION

PKD is a lethal genetic disease inherited in humans. The most striking renal feature in PKD is the presence of hundreds of fluid-filled renal cysts, which eventually destroy kidney structure and function. Two of the genes involved, PKD1 and PKD2, have been identified and cloned. Mutations of these two genes account for more than 95% of the patient population. Cyst expansion is a major factor for the progressive deterioration and loss of renal function. PKD also causes cysts to develop in liver and elsewhere in the body. In addition, the PKD also causes serious complications and problems, such as high blood pressure, kidney failure, cysts in the liver, and problems with blood vessels in brain and heart. When cysts develop in liver, it is called polycystic liver disease (PLD). The most common occurrence of PLD is associated with PKD, where patients have cysts in both the liver and kidneys. There are critical unmet needs for PKD and PLD patients.

NKA is a transmembrane enzyme responsible for the active reciprocal transport of Na⁺ and K⁺ ions across the plasma membrane of all animal cells. NKA comprises two basic subunits: the α subunit and the β subunit. The larger α subunit is the functional subunit, which catalyzes the hydrolysis of ATP for active transport of Na⁺ and K⁺ ions across the plasma membrane; the smaller β subunit does not participate in the catalytic process of the enzyme, but instead acts as a specific chaperone that assists the biogenesis and correct membrane insertion of newly synthesized NKA. The α subunit of NKA has three isoforms including α1, α2 and α3. The β subunit of NKA also has three isoforms including β1, β2 and β3. NKA plays a vitally important role in cell function. Studies have demonstrated that significant reduced NKA activity is tightly associated with PKD-induced complications including kidney failure and heart failure, demonstrating that protecting and maintaining NKA functional activity from injury is an essential new target for prevention and treatment of PKD.

BRIEF SUMMARY OF INVENTION

The inventor has surprisingly discovered that the NKA antibody agonists or activators, which target the α subunit, or the β subunit, or both of the NKA subunits, can prevent and treat PKD and its complications.

Invented methods to prevent and treat PKD patients involve, but not limited to: 1) Active immunization (vaccination) with peptide antigen/vaccine of the NKA antibody-activators to mothers prior to their pregnancy or during their pregnancy, can prevent, treat, or slow PKD formation and progression in fetus (unborn baby); 2) Active immunization with peptide antigens of the NKA antibody-activators to babies after their birth can prevent, treat, and slow PKD formation and progression; 3) Passive immunizations with NKA antibody-activator to the mothers prior to their pregnancy or during their pregnancy can prevent, treat, and slow PKD formation and progression in in fetus; 4) Passive immunizations with NKA antibody-activator to the babies after their birth can prevent, treat, and slow PKD formation and progression; 5) Both NKA activator based active and passive immunizations (also called active and passive immunotherapies) can prevent, treat, and slow the formation and progression of PKD induced kidney failure, liver problems, High blood pressure, kidney enlargement, blood in urine, and kidney stones and more.

Examples of NKA activator antibodies having α or β subunit binding specificity that can be used in the methods of the present invention include, but are not limited to, SSA78 (also referred as Jianye 2), SSA401 (also referred as KX-2), SSA412 (also referred as KX-1), JY2948, and JY421228 polyclonal, monoclonal, humanized and human version antibodies thereof, and fragments thereof. These antibodies are capable of increasing NKA enzymatic activity (activation of NKA), which are described for treating other different diseases and conditions in Patent Publication No. PCT/US2006/012912 and U.S. Pat. Nos. 9,974,842, 9,956,275, 9,790,270, 9,527,923, 9,409,949, 9,416,159, 9,238,695, 9,279,020, 9,040,046, 8,945,555, 8,496,929, 8,435,519, 8,383,111, 7,754,210, 10,053,505, 10,214,583 and 10,287,361, which are herein as reference information for all purposes.

In addition, PKD and its complications can also be treated by administration of antigenic peptide antigens (or peptide vaccine) of NKA α or β subunits that induce production of endogenous specific antibody activators against the α or β subunits of NKA and increase NKA activity. Such peptides and the administration thereof are also described for treating different diseases and conditions in U.S. Pat. Nos. 9,974,842, 9,956,275, 9,790,270, 9,527,923, 9,409,949, 9,416,159, 9,238,695, 9,279,020, 9,040,046, 8,945,555, 8,496,929, 8,435,519, 8,383,111, 7,754,210, 10,053,505, 10,214,583 and 10,287,361, which are herein incorporated as reference information for all purposes.

In a first aspect, the invention thus provides methods for preventing the formation and progression of PKD, and its complications, comprising contacting kidney cells with an antibody having binding specificity for the α or β subunit of NKA. Exemplary antibodies that may be used in these methods include, but are not limited to, (i) antibodies having binding specificity for the α or β subunit of NKA, (ii) antibodies having binding specificity for one or more of the peptides represented by SEQ ID NOs:3-7, (iii) NKA activator antibodies in a humanized or human versions thereof, or a fragment or derivative thereof, and (iv) antigens of SEQ ID NOs: 3-7 to generating endogenous NKA activator antibody, in a human or polyclonal versions thereof, or a fragment or derivative thereof. The method may be conducted in vitro or in vivo. The method may also be conducted in blood ex vivo.

In a second aspect, the invention provides methods for treating the formation and progression of PKD, and its complications, comprising contacting kidney cells with an antibody having binding specificity for the α or β subunit of NKA. Exemplary antibodies that may be used in these methods include, but are not limited to, (i) antibodies having binding specificity for the α or β subunit of NKA, (ii) antibodies having binding specificity for one or more of the peptides represented by SEQ ID NOs: 3-7, (iii) NKA activator antibodies in a humanized or human versions thereof, or a fragment or derivative thereof, and (iv) using SEQ ID NOs: 3-7 peptide antigen to generate endogenous NKA activator antibodies, in human or polyclonal versions thereof, or a fragment or derivative thereof. The method may be conducted in vitro or in vivo. The method may also be conducted in blood ex vivo.

In a third aspect, the invention provides methods for inhibiting PKD in a subject comprising administering an effective amount of an antibody having binding specificity for the α or β subunit of NKA to a subject in need thereof. Exemplary antibodies that may be used in these methods include, but are not limited to, (i) antibodies having binding specificity for the α or β subunit of NKA, (ii) antibodies having binding specificity for one or more of the peptides represented by SEQ ID NOs: 3-7, (iii) NKA activator antibodies in a humanized or human versions thereof, or a fragment or derivative thereof, and (iv) using SEQ ID NOs: 3-7 peptide antigen to generate endogenous NKA activator antibodies, in human or polyclonal versions thereof, or a fragment or derivative thereof. The subject may be one that is characterized has having or at being at greater risk than the general population for PKD and its complications.

In a fourth aspect, the invention provides methods for protecting kidney structure/function and preventing kidney failure in a subject comprising administering an effective amount of an antibody having binding specificity for the α or β subunit of NKA to a subject in need thereof. Exemplary antibodies that may be used in these methods include, but are not limited to, (i) antibodies having binding specificity for the α or β subunit of NKA, (ii) antibodies having binding specificity for one or more of the peptides represented by SEQ ID NOs:3-7, (iii) NKA activator antibodies in a humanized or human versions thereof, or a fragment or derivative thereof, and (iv) using SEQ ID NOs: 3-7 peptide antigen to generate endogenous NKA activator antibodies, in human or polyclonal versions thereof, or a fragment or derivative thereof. The subject may one that is at greater risk than the general population for kidney failure. The subject may be one that is characterized has having or at being at greater risk than the general population for one or more of the following diseases and conditions: PKD, high blood pressure, abnormal renal architecture, renal insufficiency, loss of kidney function, chronic pain, growth of cysts in the liver, development of an aneurysm, pregnancy complications, heart valve abnormalities, heart disease, colon problems, kidney failure, and irreversible end-stage kidney disease, which requires a kidney transplant.

In a fifth aspect, the invention provides methods for treating PKD induced complications in a subject comprising administering an effective amount of an antibody having binding specificity for the α subunit of NKA to a subject in need thereof. Exemplary antibodies that may be used in these methods include, but are not limited to, (i) antibodies having binding specificity for the α subunit of NKA, (ii) antibodies having binding specificity for one or more of the peptides antigen or peptide vaccine represented by SEQ ID NOs:3-7, (iii) NKA activator antibodies in a humanized or human versions thereof, or a fragment or derivative thereof, and (iv) using SEQ ID NOs: 3-7 peptide antigen to generate endogenous NKA activator antibodies, in human or polyclonal versions thereof, or a fragment or derivative thereof. The subject may be one that is characterized has having or at being at greater risk than the general population for one or more of the following diseases and conditions: PKD, high blood pressure, abnormal renal architecture, renal insufficiency, loss of kidney function, chronic pain, growth of cysts in the liver, development of an aneurysm, pregnancy complications, heart valve abnormalities, heart disease, colon problems, kidney failure, and irreversible end-stage kidney disease, which requires a kidney transplant, or other disease or condition wherein inhibition of PKD would be desirable or necessary.

In a sixth aspect, the invention provides methods for treating or slowing PKD progression in a subject comprising administering an effective amount of an antibody having binding specificity for the α or β subunit of NKA to a subject in need thereof. Exemplary antibodies that may be used in these methods include, but are not limited to, (i) antibodies having binding specificity for the α or β subunit of NKA, (ii) antibodies having binding specificity for one or more of the peptides represented by SEQ ID NOs:3-7 (iii) NKA activator antibodies in a humanized or human versions thereof, or a fragment or derivative thereof, and (iv) using SEQ ID NOs: 3-7 peptide antigen to generate endogenous NKA activator antibodies, in human or polyclonal versions thereof, or a fragment or derivative thereof. The subject may be one that is characterized has having or at being at greater risk than the general population for one or more of the following diseases and conditions: PKD, high blood pressure, abnormal renal architecture, renal insufficiency, loss of kidney function, chronic pain, growth of cysts in the liver, development of an aneurysm, pregnancy complications, heart valve abnormalities, heart disease, colon problems, kidney failure, and irreversible end-stage kidney disease, which requires a kidney transplant, or other disease or condition wherein inhibition of PKD would be desirable or necessary.

In a seventh aspect, the invention provides methods for preventing and treating cysts growth induced kidney enlargement in a subject comprising administering an effective amount of an antibody having binding specificity for the α or β subunit of NKA to a subject in need thereof. Exemplary antibodies that may be used in these methods include, but are not limited to, (i) antibodies having binding specificity for the α or β subunit of NKA, (ii) antibodies having binding specificity for one or more of the peptides represented by SEQ ID NOs:3-7, (iii) NKA activator antibodies in a humanized or human versions thereof, or a fragment or derivative thereof, and (iv) using SEQ ID NOs: 3-7 peptide antigen to generate endogenous NKA activator antibodies, in human or polyclonal or monoclonal versions thereof, or a fragment or derivative thereof. Exemplary diseases include, but are not limited to, PKD, high blood pressure, abnormal renal architecture, renal insufficiency, loss of kidney function, chronic pain, growth of cysts in the liver, development of an aneurysm, pregnancy complications, heart valve abnormalities, heart disease, colon problems, kidney failure, and irreversible end-stage kidney disease, which requires a kidney transplant, or other disease or condition wherein inhibition of PKD would be desirable or necessary.

In an eighth aspect, the invention provides methods for prolonging life span for PKD patient comprising administering an effective amount of an antibody having binding specificity for the α or β subunit of NKA to a subject in need thereof. Exemplary antibodies that may be used in these methods include, but are not limited to, (i) antibodies having binding specificity for the α or β subunit of NKA, (ii) antibodies having binding specificity for one or more of the peptides represented by SEQ ID NOs:3-7, (iii) NKA activator antibodies in a humanized or human versions thereof, or a fragment or derivative thereof, and (iv) using SEQ ID NOs: 3-7 peptide antigen to generate endogenous NKA activator antibodies, in human or polyclonal or monoclonal versions thereof, or a fragment or derivative thereof.

In each of these aspects, the antibody may be in a pharmaceutical formulation comprising the antibody and a pharmaceutically acceptable carrier.

The foregoing has outlined rather broadly the features and technical advantages of the present invention in order that the detailed description of the invention that follows may be better understood. Additional features and advantages of the invention will be described herein, which form the subject matter of the claims of the invention.

BRIEF DESCRIPTION OF DRAWINGS

FIG. 2. Evidence that rapid cyst growth starts in fetus mice kidney and endogenous NKA SSA412 protected fetus kidney structure and function and significantly slowed the rate of rapid cyst growth. Mother mice were prepared with (FIG. 2C) or without (FIG. 2B) NKA peptide antigen/vaccine immunizations. FIG. 2A represents the control. Kidneys were collected from newborn (Day-0) mice within 1-2 hours of their birth. Experiment results show that active immunization generated endogenous NK SSA412 significantly protected PKD1$^{v/v}$ kidney structure and function in newborn mice against the rapid progressive cyst growth. In contrast, rapid cyst growth occurred in fetus PKD1$^{v/v}$ mice kidney (FIG. 2B) without NKA peptide antigen/vaccine immunization (n=15/condition).

FIG. 3. Evidence that endogenous SSA412 antibody significantly protected Day-6 kidney structure and function against rate of rapid cyst growth. Mother mice were prepared with (FIG. 3C) or without (FIG. 3B) NKA peptide antigen/vaccine immunizations. FIG. 3A represents the control. Kidneys were collected 6 days after birth. FIG. 3C provides evidence to demonstrate the biological capability of endogenous SSA412 antibody through providing powerful protection on PKD kidney structure and function (FIG. 3) and function (FIG. 4) against cysts formation during mother mice pregnancy, before and after pups' birth. In strong contrast, rapid cyst growth occurred in untreated Day-6 PKD1$^{v/v}$ mice kidneys (FIG. 3B) compared with the control wild type mice kidneys (FIG. 3A) (n=15/condition).

FIG. 6. Evidence that endogenous SSA412 antibody can be successfully generated in PKD mother mice and naturally transferred to their pups. Animal blood was collected from mother mice and D-0 pups. Serum was isolated for ELISA analysis. FIG. 6 provides direct ELISA evidence showing the generation of endogenous SSA412 antibody in mother mice (FIG. 6A), where the similar concentration of endogenous SSA412 antibody (FIG. 6B) was then naturally transferred from mother mice to pups through blood circulation during the mother mice pregnancy, which provided critical protection on structure and function of pups' kidney (FIGS. 2C & 3C). These PKD1$^{v/v}$ pups are considered "treated mice" since their blood contains endogenous SSA412 antibody. The process of passing IgG endogenous SSA412 antibody from mother mice to a fetus throughout pregnancy is called passive immunity. These data further demonstrate the powerful biological action of both peptide vaccine pNKAab$^{412}$ and the endogenous SSA412 antibody generation in PKD1$^{v/v}$ mice.

DETAILED DESCRIPTION OF THE INVENTION

Figure 1A:
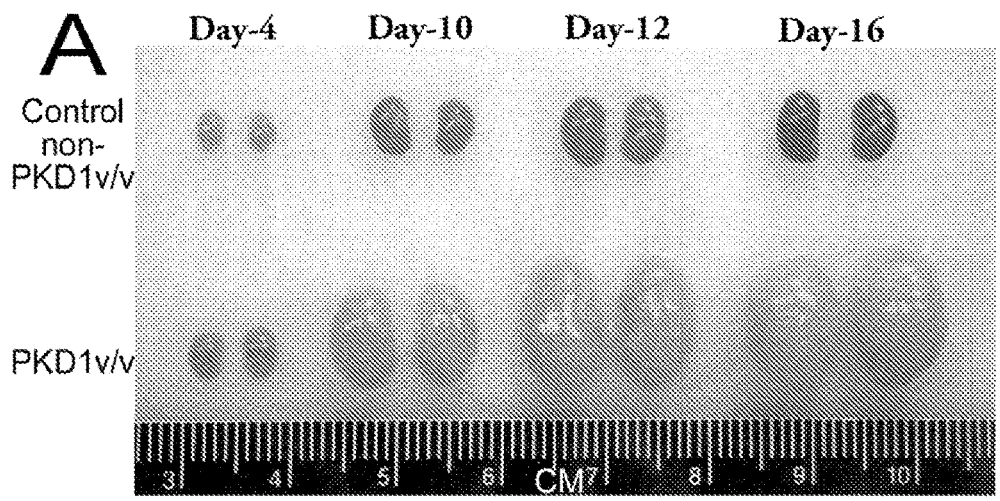
FIG. 1. PKD mice kidney NKA activity comparisons between control and PKD1 mice. Mice models were purchased from the Baltimore PKD Foundation. Mice kidneys were collected on days 2, 4, 10, 12, and 16 from non-PKD1$^{v/v}$ (wild type: wt) control and PKD1$^{v/v}$. The kidney NKA activities were then determined and compared. Experimental results reveal that the NKA activity in PKD1$^{v/v}$ kidney was significantly decreased to 10% in 16 days after the birth [Figure (FIG.) 1B, open-circle], which is consistent with the progressive kidney enlargement shown in FIG. 1A. The findings demonstrate that a substantial reduction of NKA activity within the enlarged PKD kidneys (FIG. 1B) and suggest that impaired NKA function participates in and contributes to the mechanism of the progressive enlargement of fluid-filled cysts. The findings further suggest that the dysfunction of NKA may play a critical role in the driving force of cyst fluid accumulation.
Figure 1B:
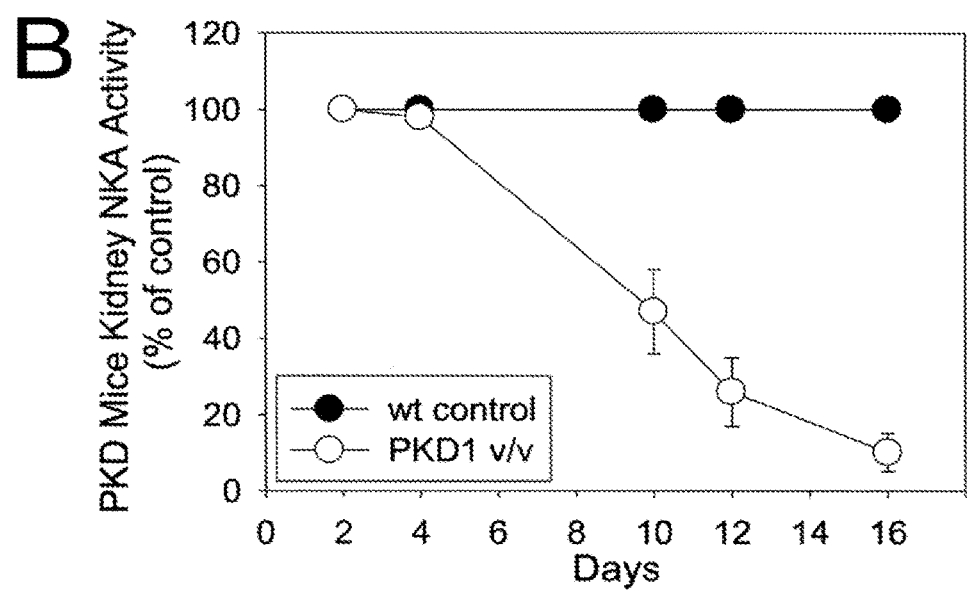

Unless otherwise noted, technical terms are used according to conventional usage. Definitions of common terms in molecular biology may be found, for example, in Benjamin Lewin, Genes VII, published by Oxford University Press, 2000 (ISBN 019879276X); Kendrew et al. (eds.); The Encyclopedia of Molecular Biology, published by Blackwell Publishers, 1994 (ISBN 0632021829); and Robert A. Meyers (ed.), Molecular Biology and Biotechnology: a Comprehensive Desk Reference, published by Wiley, John & Sons, Inc., 1995 (ISBN 0471186341); and other similar technical references.

As used herein, "a" or "an" may mean one or more. As used herein when used in conjunction with the word "comprising," the words "a" or "an" may mean one or more than one. As used herein "another" may mean at least a second or more. Furthermore, unless otherwise required by context, singular terms include pluralities and plural terms include the singular.

As used herein, "about" refers to a numeric value, including, for example, whole numbers, fractions, and percentages, whether or not explicitly indicated. The term "about" generally refers to a range of numerical values (e.g., +/−5-10% of the recited value) that one of ordinary skill in the art would consider equivalent to the recited value (e.g., having the same function or result). In some instances, the term "about" may include numerical values that are rounded to the nearest significant figure.

As outlined in a general manner above, the present invention is based on the surprising discovery that NKA antibody agonists or activators with α or β subunit activation site binding specificity can be used to protect insulin-producing β cell function, inhibit hyperglycemia, prevent and treat hyperglycemia caused kidney failure, heart failure, protein damages and other dangerous complications in a subject. Such NKA activator antibodies thus form the basis of methods of treating or preventing PKD associated with diseases, whether in vitro or in vivo, to inhibit, treat, and prevent PKD and its complications in a subject. The antibodies and their peptide antigens also form the basis of methods of treating or preventing PKD, and their associated diseases and complications.

Antibodies

The skilled artisan will understand that the particular attributes of the antibodies that may be used in the methods of the present invention are only confined by (i) the ability to bind with specificity to the α or β subunit of NKA, and (ii) the ability to inhibit PKD or PLD and their complications As described in PCT/US2006/012912 and U.S. Pat. Nos. 9,974,842, 9,956,275, 9,790,270, 9,527,923, 9,409,949, 9,416,159, 9,238,695, 9,279,020, 9,040,046, 8,945,555, 8,496,929, 8,435,519, 8,383,111, 7,754,210, 10,053,505, 10,214,583 and 10,287,361, five antibodies have been prepared that specifically bind the α or β subunit of NKA for treating different diseases. The following antibodies specifically bind to the α subunit of NKA, namely antibody SSA78 (also referred as Jianye 2 antibody), SSA401 (also referred as KX-2 antibody), and SSA412 (also referred as KX-1 antibody). Antibodies JY2948 and JY421228 specifically bind to the β subunit of NKA. As shown in the Examples below, these antibodies may be used in the methods of the present invention. SSA78 binds to amino acids RSATEEEPPNDD (SEQ ID NO:3), SSA401 binds to amino acids HLLGIRETWDDRWIN (SEQ ID NO:4), SSA412 binds to amino acids DVEDSYGQQWTYEQR (SEQ ID NO:5), JY2948 binds to amino acids KERGEFNHERGER (SEQ ID NO:6), and JY421228 binds to amino acids RDEDKDKVGNIEY (SEQ ID NO:7). The invention therefore provides the use of NKA activator antibodies SSA78, SSA401, SSA412, JY2948, and antibody JY421228 in the methods disclosed herein.

The invention also provides the use of antibodies that specifically bind an epitope of the α or β subunit of NKA comprising the amino acid sequence RSATEEEPPNDD (SEQ ID NO:3), HLLGIRETWDDRWIN (SEQ ID NO:4), DVEDSYGQQWTYEQR (SEQ ID NO:5), KERGEFNHERGER (SEQ ID NO:6), and RDEDKDKVGNIEY (SEQ ID NO:7), or any combination thereof.

The invention further provides for the use of antibodies having binding specificity for an epitope of the α or β subunit of NKA comprising the amino acid SEQ ID NOs: 3-7. Antibody SSA78 binds to amino acids RSATEEEPPNDD (SEQ ID NO:3), SSA401 binds to amino acids HLLGIRETWDDRWIN (SEQ ID NO:4), SSA412 binds to amino acids DVEDSYGQQWTYEQR (SEQ ID NO:5), JY2948 binds to amino acids KERGEFNHERGER (SEQ ID NO:6), and JY421228 binds to amino acids RDEDKDKVGNIEY (SEQ ID NO:7).

The invention further provides for the use of antibodies having binding specificity for variants of each of the peptides of SEQ ID NOs:3-7, the variants having 8 or fewer, 5 or fewer, 4 or fewer, 3 or fewer, 2 or fewer, or 1 amino acid change in comparison to the peptides of SEQ ID NOs:3-7. The changes are each individually selected from insertions, deletions and substitutions. The substitutions may be conservative or non-conservative amino acid substitutions. Each of the variant peptides maintains the ability to induce production of antibodies that specifically bind the α or β subunit of NKA and that have the ability to inhibit PKD and PLD complications.

In addition, the invention provides for the use of antibodies having binding specificity for other epitopes of the α and β subunit of NKA, with those antibodies having binding specificity for other epitopes of the α or β subunit of NKA being of particular note.

The antibodies used in the methods of the present invention and defined above may be polyclonal, monoclonal, humanized, chimeric antibodies, or human version, and the antibodies may be in the form of an antiserum comprising the antibodies. The antibodies may be of any class, such as IgG1, IgG2, IgG3, IgG4, IgM, IgA1, IgA2, IgD or IgE. The antibodies may be isolated antibodies, purified antibodies, exogenous antibodies, endogenous antibodies, single chain antibodies, single-chain variable fragment, or a combination thereof.

The antibodies may also be antibody fragments of less than the entire antibody, including, but not limited to, single chain antibodies, F(ab')$_2$ fragments, Fab fragments, and fragments produced by an Fab expression library, and derivatives of the antibodies and fragments defined herein, with the only limitation being that the antibody fragments and derivatives retain the ability to bind the α or β subunit and inhibit PKD or PLD and its complications. It will thus be clear to the skilled artisan that all references to "antibodies" herein include both full-size antibodies as well as antibody fragments, as defined herein.

The antibodies may be produced in any species of animal, though preferably from a mammal such as a human, simian, mouse, rat, rabbit, guinea pig, horse, cow, sheep, goat, pig, dog or cat. For example, the antibodies can be human antibodies or humanized antibodies, or any antibody preparation suitable for administration to a human. For the production of the antibodies, the selected species of animal can be immunized by injection with one or more of the peptides or variants discussed herein. The peptides and variants may be administered in conjunction with one or more pharmaceutically acceptable adjuvants to increase the immunological response. Suitable adjuvants include, but are not limited to, Freund's Complete and Incomplete Adjuvant, Titermax, Oil in Water Adjuvants, as well as Aluminum compounds where antigens, normally peptides, are physically precipitated with hydrated insoluble salts of aluminum hydroxide or aluminum phosphate. Other adjuvants include liposome-type adjuvants comprising spheres having phospholipid bilayers that form an aqueous compartment containing the peptide and protect it from rapid degradation, and that provide a depot effect for sustained release. Surface active agents may also be used as adjuvants and include lipoteichoic acid of gram-positive organisms, lipid A, and TDM. Quil A and QS-21 (saponin-type adjuvants), monophosphoryl lipid A, and lipophilic MDP derivatives are suitable adjuvants that have hydrophilic and hydrophobic domains from which their surface-active properties arise. Compounds normally found in the body such as vitamin A and E, and lysolecithin may also be used as surface-active agents. Other classes of adjuvants include glycan analog, coenzyme Q, amphotericin B, dimethyldioctadecylammonium bromide (DDA), levamisole, and benzimidazole compounds. The immunostimulation provided by a surface active agent may also be accomplished by either developing a fusion protein with non-active portions of the cholera toxin, exotoxin A, or the heat labile toxin from *E. coli*. Immunomodulation through the use of anti-IL-17, anti IFN-γ, anti-IL-12, IL-2, IL-10, or IL-4 may also be used to promote a strong Th2 or antibody mediated response to the immunogenic formulation.

Means for preparing antibodies are very well known in the art. The antibodies of the invention can be prepared using any known technique that provides for the production of antibody molecules. Suitable techniques include, but are not limited to, the hybridoma technique originally described by Koehler and Milstein (Nature 256:495-497 (1975)), the human B-cell hybridoma technique (Kosbor et al., Immunol Today 4:72 (1983); Cote et al., Proc Natl. Acad. Sci 80:2026-2030 (1983)), and the EBV-hybridoma technique (Cole et al., Monoclonal Antibodies and Cancer Therapy, Alan R. Liss Inc, New York N.Y., pp 77-96 (1985)). Each of these publications is herein incorporated by reference in its entirety. Additionally, antibodies can be produced by inducing in vivo production in the lymphocyte population or by screening recombinant immunoglobulin libraries or panels of highly specific binding reagents as disclosed in Orlandi et al., *Proc Natl. Acad. Sci. USA* 86: 3833-3837 (1989), and in Winter G. and Milstein C., *Nature* 349:293-299 (1991), both of which is herein incorporated by reference in its entirety.

Humanized antibodies are those where a human antibody has been engineered to contain non-human complementarity-determining regions (CDRs) derived from an antibody produced in a non-human host against a selected antigen. Means for producing humanized antibodies are well-known in the art and include Vaswani S K, and Hamilton R G, *Ann Allergy Asthma Immunol.* 81(2):105-15 (1998) and Kashmiri S V et al., *Methods* 36 (1):25-34 (2005), each of which is herein incorporated by reference in its entirety.

Human antibodies are those where an antibody produced in a non-human host against a selected antigen. Means for producing human antibodies are well-known in the art and include Bruggemann M et al., *Arch Immunol Ther Exp* (*Warsz*). 63(2):101-108 (2014), Pruzina S et al., *Protein Eng Des Sel.* 24 (10):791-799 (2011), and Smith K et al., *Nature.* 4:372-384 (2009), each of which is herein incorporated by reference in its entirety.

Chimeric antibodies are those where an antigen binding region (e.g., $F(ab')_2$ or hypervariable region) of a non-human antibody is transferred into the framework of a human antibody by recombinant DNA techniques. Techniques developed for the production of such antibodies include the splicing of mouse antibody genes to human antibody genes to obtain a molecule with appropriate antigen specificity and biological activity. Such techniques are also well known and include: Morrison et al., *Proc Natl. Acad. Sci* 81:6851-6855 (1984); Neuberger et al., *Nature* 312:604-608(1984); Takeda et al., *Nature* 314:452-454(1985), each of which is herein incorporated by reference in its entirety.

Techniques for the production of single chain antibodies are described in in U.S. Pat. No. 4,946,778, incorporated herein by reference in its entirety.

Antibody fragments such as $F(ab')_2$ fragments can be produced by pepsin digestion of the antibody molecule, and Fab fragments can be generated by reducing the disulfide bridges of the $F(ab')_2$ fragments. Alternatively, Fab expression libraries can be constructed to allow rapid and easy identification of monoclonal Fab fragments with the desired specificity (Huse W. D. et al., Science 256:1275-1281 (1989), herein incorporated by reference in its entirety).

The invention provides for the use of pharmaceutical formulations comprising one or more of the antibodies of the invention and a pharmaceutically acceptable carrier. Such formulations may be administered to a subject when practicing the methods of the present invention. Suitable examples of carriers are well known to those skilled in the art and include water, water-for-injection, saline, buffered saline, dextrose, glycerol, ethanol, propylene glycol, polysorbate 80 (Tween-80™), poly(ethylene)glycol 300 and 400 (PEG 300 and 400), PEGylated castor oil (e.g. Cremophor EL), poloxamer 407 and 188, hydrophilic and hydrophobic carriers, and combinations thereof. Hydrophobic carriers include, for example, fat emulsions, lipids, PEGylated phospholipids, polymer matrices, biocompatible polymers, lipospheres, vesicles, particles, and liposomes. The terms specifically exclude cell culture medium. The formulations may further comprise stabilizing agents, buffers, antioxidants and preservatives, tonicity agents, bulking agents, emulsifiers, suspending or viscosity agents, inert diluents, fillers, and combinations thereof.

The identity of the carrier(s) will also depend on the means used to administer pharmaceutical formulations comprising antibodies to a subject. For example, pharmaceutical formulations for intramuscular preparations can be prepared where the carrier is water-for-injection, 0.9% saline, or 5% glucose solution. Pharmaceutical formulations may also be prepared as liquid or powdered atomized dispersions for delivery by inhalation. Such dispersion typically contain carriers common for atomized or aerosolized dispersions, such as buffered saline and/or other compounds well known to those of skill in the art. The delivery of the pharmaceutical formulations via inhalation has the effect of rapidly dispersing the vaccine formulation to a large area of mucosal tissues as well as quick absorption by the blood for circulation. One example of a method of preparing an atomized dispersion is described in U.S. Pat. No. 6,187,344, entitled, "Powdered Pharmaceutical Formulations Having Improved Dispersibility," which is hereby incorporated by reference in its entirety.

Additionally, the pharmaceutical formulations may also be administered in a liquid form. The liquid can be for oral dosage, for ophthalmic or nasal dosage as drops, or for use as an enema or douche. When the pharmaceutical formulation is formulated as a liquid, the liquid can be either a solution or a suspension of the pharmaceutical formulation. There is a variety of suitable formulations for the solution or suspension of the pharmaceutical formulations that are well known to those of skill in the art, depending on the intended use thereof. Liquid formulations for oral administration prepared in water or other aqueous vehicles may contain various suspending agents such as methylcellulose, alginates, tragacanth, pectin, kelgin, carrageenan, acacia, polyvinylpyrrolidone, and polyvinyl alcohol. The liquid formulations may also include solutions, emulsions, syrups and elixirs containing, together with the active compound(s), wetting agents, sweeteners, and coloring and flavoring agents.

The invention also includes inhibiting PKD or PLD and its complications by administering a peptide vaccine that includes one or more peptides selected from a group of peptides having the amino acid sequences RSATEEEPPNDD (SEQ ID NO:3), HLLGIRETWDDRWIN (SEQ ID NO:4), DVEDSYGQQWTYEQR (SEQ ID NO:5), KERGEFNHERGER (SEQ ID NO:6), and RDEDKDKVGNIEY (SEQ ID NO:7), and variants or fragments thereof. These peptides represent antigenic determinants or epitopes on the a or 3 subunit of NKA. The peptide vaccines stimulate the host immune system to generate antibodies against the respective one or more peptide epitopes. Methods of using peptide antigen for making, isolating and purifying NKA activity-increasing antibodies and the above-identified peptide antigenic determinants are described in U.S. Patent Applications 20040057956 and 20030228315, the entire contents of which are hereby incorporated by reference as if fully set forth herein.

Methods for Inhibiting PKD

As indicated above, the present invention includes methods for inhibiting PKD or PLD and its complications. This method comprising contacting kidney or liver cells with an antibody having binding specificity for the α or β subunit of NKA. It will be apparent to the skilled artisan that this method can be practice in vitro, in vivo and ex vivo.

Any of the antibodies described herein, whether polyclonal or monoclonal, can be used in the method, as well as humanized or chimeric versions or human versions of the antibodies, and fragments of any of these. Exemplary antibodies that may be used in these methods include, but are not limited to, (i) antibodies having binding specificity for the α or β subunit of NKA, (ii) antibodies having binding specificity for one or more of the peptides represented by SEQ ID NOs: 3-7, (iii) antibodies in polyclonal, monoclonal, humanized and human versions thereof, and (iv) antibodies in an exogenous or endogenous versions thereof.

Methods for Inhibiting PKD Induced Complications

The present invention includes methods for inhibiting PKD complications. This method comprising contacting kidney cells with an antibody having binding specificity for the α or β subunit of NKA. It will be apparent to the skilled artisan that this method can be practice in vitro, in vivo and ex vivo.

Any of the antibodies described herein, whether polyclonal or monoclonal, can be used in the method, as well as humanized or human version of the antibodies, and fragments of any of these. Exemplary antibodies that may be used in these methods include, but are not limited to, (i) antibodies having binding specificity for the α or β subunit of NKA, (ii) antibodies having binding specificity for one or more of the peptides represented by SEQ ID NOs:3-7, (iii) antibodies polyclonal, monoclonal, humanized and human versions thereof, and (iv) antibodies in an exogenous or endogenous versions thereof.

Methods of Treatment

The invention also provides methods for treating or preventing particular diseases, disorders and conditions in a subject by inhibiting PKD.

The invention thus includes methods for inhibiting PKD complications in a subject comprising administering an effective amount of an antibody having binding specificity for the α or β subunit of NKA to a subject in need thereof. While the subject is not limited to one having a particular disease or condition, the subject may be one that is characterized has having or at being at greater risk than the general population for one or more of the following diseases and conditions: PKD, high blood pressure, abnormal renal architecture, renal insufficiency, loss of kidney function, chronic pain, growth of cysts in the liver, development of an aneurysm, pregnancy complications, heart valve abnormalities, heart disease, colon problems, kidney failure, and irreversible end-stage kidney disease, which requires a kidney transplant, or other disease or condition wherein inhibition of PKD would be desirable or necessary.

The invention includes methods for inhibiting, treating or preventing PKD and its complications in a subject, where the method comprises administering an effective amount of an antibody having binding specificity for the α or β subunit of NKA to a subject in need thereof. While the subject is not limited to one having a particular disease or condition, the subject may be one that is characterized as having or at being at greater risk than the general population for one or more of the following diseases and conditions: PKD, high blood pressure, abnormal renal architecture, renal insufficiency, loss of kidney function, chronic pain, growth of cysts in the liver, development of an aneurysm, pregnancy complications, heart valve abnormalities, heart disease, colon problems, kidney failure, and irreversible end-stage kidney disease, which requires a kidney transplant, or other disease or condition wherein inhibition of PKD would be desirable or necessary.

Any of the antibodies described herein, whether polyclonal or monoclonal, can be used in the method, as well as humanized or chimeric or human versions of the antibodies, and fragments and derivatives of any of these. Exemplary antibodies that may be used in these methods include, but are not limited to, (i) antibodies having binding specificity for the α or β subunit of NKA, including isoform of α and β subunit, (ii) antibodies having binding specificity for one or more of the peptides represented by SEQ ID NOs:3-7, (iii) antibodies in a polyclonal, monoclonal, humanized or human versions thereof, or a fragment, or single-chain antibody, or single-chain variable fragment, or derivative thereof, and (iv) antibodies in an exogenous or endogenous versions thereof, or a fragment or derivative thereof. The antibody may be administered as a pharmaceutical formulation comprising the antibody and a pharmaceutically acceptable carrier.

As used herein, the terms "treat", "treating" and "treatment" have their ordinary and customary meanings, and include one or more of, ameliorating PKD, ameliorating a symptom of PKD complications, or decreasing in severity and/or frequency a symptom of PKD complications. Treatment means ameliorating or decreasing by about 1% to about 100% versus a subject to which the antibody has not been administered. Preferably, the ameliorating or decreasing or inhibiting is about 100%, about 99%, about 98%, about 97%, about 96%, about 95%, about 90%, about 80%, about 70%, about 60%, about 50%, about 40%, about 30%, about 20%, about 10%, about 5% or about 1%. The treatment may begin prior to, concurrent with, or after the onset of clinical symptoms of PKD and PKD complications. The results of the treatment may be permanent or may continue for a period of days (such as 1, 2, 3, 4, 5, 6 or 7 days), weeks (such as 1, 2, 3 or 4 weeks) or months (such as 1, 2, 3, 4, 5, 6 or more months).

As used herein, the terms "prevent", "preventing" and "prevention" have their ordinary and customary meanings, and include one or more of, stopping, averting, avoiding or blocking PKD and its complications, the occurrence of a symptom of PKD and its complications, the recurrence of a symptom of PKD and its complications, the development of PKD and its complications or the progression of PKD and its complications. Prevention means stopping by at least about 95% versus a subject to which the antibody has not been administered. Preferably, the stopping is about 100%, about 99%, about 98%, about 97%, about 96% or about 95%. The results of the prevention may be permanent or may continue for a period of days (such as 1, 2, 3, 4, 5, 6 or 7 days), weeks (such as 1, 2, 3 or 4 weeks) or months (such as 1, 2, 3, 4, 5, 6 or more months).

As used herein, the terms "inhibit", "inhibiting" and "inhibition" have their ordinary and customary meanings, and include one or more of, hindering, impeding, obstructing, deterring or restraining PKD and its complications, the occurrence of a symptom of PKD and its complications, the recurrence of a symptom of PKD and its complications, the development of PKD and its complications, or the progression of PKD and its complications. Inhibition means impeding by about 1% to about 100% versus a subject to which the antibody has not been administered. Preferably, the impeding is about 100%, about 99%, about 98%, about 97%, about 96%, about 95%, about 90%, about 80%, about 70%, about 60%, about 50%, about 40%, about 30%, about 20%, about 10%, about 5% or about 1%. The course of therapy may begin prior to, concurrent with, or after the onset of clinical symptoms of PKD and its complications. Thus, the subject may have PKD and its complications, or merely be susceptible to PKD and its complications. The results of the inhibition may be permanent or may continue for a period of days (such as 1, 2, 3, 4, 5, 6 or 7 days), weeks (such as 1, 2, 3 or 4 weeks) or months (such as 1, 2, 3, 4, 5, 6 or more months).

The antibodies and formulations may be administered to a subject using different schedules, depending on the particular aim or goal of the method; the age and size of the subject; and the general health of the subject, to name only a few factors to be considered. In general, the antibodies and formulations may be administered once, or twice, three times, four times, five times, six times or more, over a course of treatment, inhibition or prevention. The timing between each dose in a dosing schedule may range between days, weeks, months, or years, an includes administered once every 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more weeks. The same quantity of antibody may be administered in each dose of the dosing schedule, or the amounts in each dose may vary. The identity of the particular antibody may also vary or remain the same in each dose in a dosing schedule.

In each of the methods of the present invention, an "effective amount" of an antibody or a pharmaceutical formulation comprising an antibody is administered to a subject. The effective amount will vary between subjects. However, the effective amount is one that is sufficient to achieve the aim or goal of the method, whether inhibiting, treating or preventing. As an example, an effective amount of an antibody used in the methods of the invention is typically between about 0.1 µg to about 1000 µg of antibody per kg of body weight of the subject to which the antibody is administered. An effective amount also includes between about 1 µg to about 500 µg, between about 10 µg to about 200 µg, between about 1 µg to about 800 µg, between about 10 µg to about 800 µg, between about 1 µg to about 300 µg, and between about 10 µg to about 300 µg of antibody per kg of body weight of the subject.

Appropriate doses and dosing schedules can readily be determined by techniques well known to those of ordinary skill in the art without undue experimentation. Such a determination will be based, in part, on the tolerability and efficacy of a particular dose.

Administration of the antibody or formulation may be via any of the means commonly known in the art of antibody delivery. Such routes include intravenous, intraperitoneal, intramuscular, subcutaneous and intradermal routes of administration, as well as nasal application, by inhalation, ophthalmically, orally, rectally, vaginally, or by any other mode that results in the antibody or formulation contacting mucosal tissues.

The term "subject" is intended to mean an animal, such birds or mammals, including humans and animals of veterinary or agricultural importance, such as dogs, cats, horses, sheep, goats, and cattle.

A kit comprising the necessary components for practicing the methods of the invention, including an antibody or a pharmaceutical formulation comprising an antibody, and instructions for its use is also within the purview of the present invention.

It is understood that the examples and embodiments described herein are for illustrative purposes only and that various modifications or changes in light thereof will be suggested to persons skilled in the art and are to be included within the spirit and purview of this application and scope of the appended claims.

All documents, papers and published materials referenced herein, including books, journal articles, manuals, patent applications, published patent applications and patents, are expressly incorporated herein by reference in their entireties.

EXAMPLES

Inhibition of PKD and PKD Induced Complications

Figure 4:
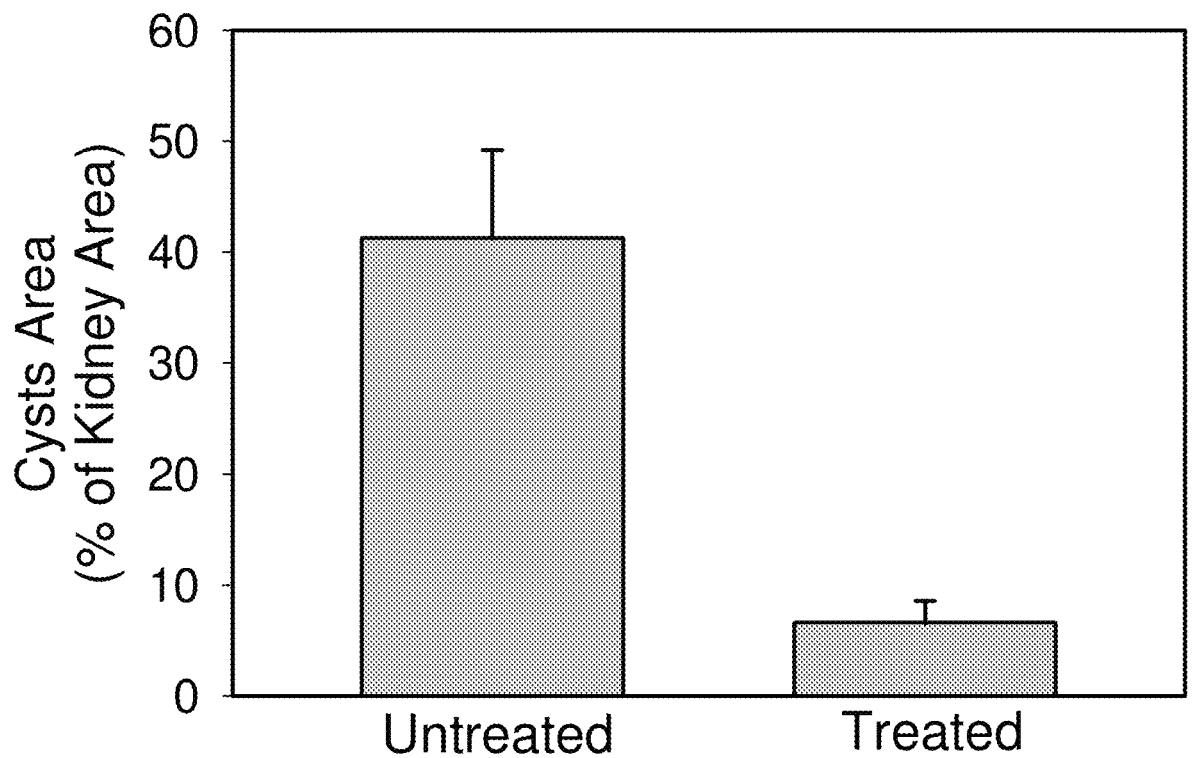
FIG. 4. ImageJ cysts area analyses between untreated and treated Day-6 PKD1$^{v/v}$ mice kidneys. Efficacy of immunization was calculated using vaccine efficacy formula: VE=Untreated group—Treated group/Untreated group× 100% (Orenstein W A, Bernier R H, Dondero T J, Hinman A R, Marks J S, Bart K J, Sirotkin B (1985). "Field evaluation of vaccine efficacy". Bull. World Health Organ. 63 (6): 1055-68.) The ImageJ analyses reveal that the cysts area of untreated kidneys was 41.2±8% (n=15) and 6.62±2% (n=15) for treated group. The ImageJ analyses estimated efficacy is 84%. Experiment data are expressed as mean±SE. There is a statistically significant difference between untreated and treated PKD1$^{v/v}$ mice (p<0.001).

Materials: Baltimore PKD Foundation PKD1 female and male mice, synthetic peptide antigens for generating different endogenous NKA activator antibodies in PKD mice. Method-1: Preparation of active immunization: Specific peptide antigens were synthesized and purified by HPLC. The purified peptides were sterilized and mixed with Titer-Max® adjuvant individually at a 1:1 volume ratio and injected (IM) to the mice monthly. Method-2: Detection of antibody generation: Serum was collected from blood and incubated with peptide antigens made against specific binding site for SSA78, SSA401, SSA412, JY2948 and JY421228 antibodies separately. ELISA was performed to determine antibody generation. Method-3: Detection of blood glucose: NOD mice blood glucose was measured weekly using OneTouch system. Method-4: Detection of urine creatinine concentration: Urine samples were collected from D-6 control, untreated, and vaccine immunotherapy treated mice and assayed using mouse creatinine assay kit (Crystal Chem, Catalog #80350). Method-5 Detection of Serum creatinine concentration: Serum creatinine was determined using Creatinine Assay Kit (abeam). Method-6: Detection of NKA activator endogenous antibodies protected kidney function and inhibit PKD and PKD complications. FIGS. 2-5 reveals NKA antibody activator-treated PKD mice and demonstrate a protective effect of NKA antibody activators on the structure and function of kidney cells. FIG. 2-5 shows SSA412 protected kidney cell function. The statistically significant difference between treated and untreated groups is p<0.001. FIG. 3 reveals NKA antibody activator-based immunotherapy significantly protected kidney function and critically prevented rapid cysts growth in PKD1$^{v/v}$ mice (p<0.001). FIG. 4 reveals that the group of mice treated with NKA antibody activator SSA412 has a statistically significant efficacy, demonstrating NKA antibody activators prolong life span of PKD mice.

Figure 5:
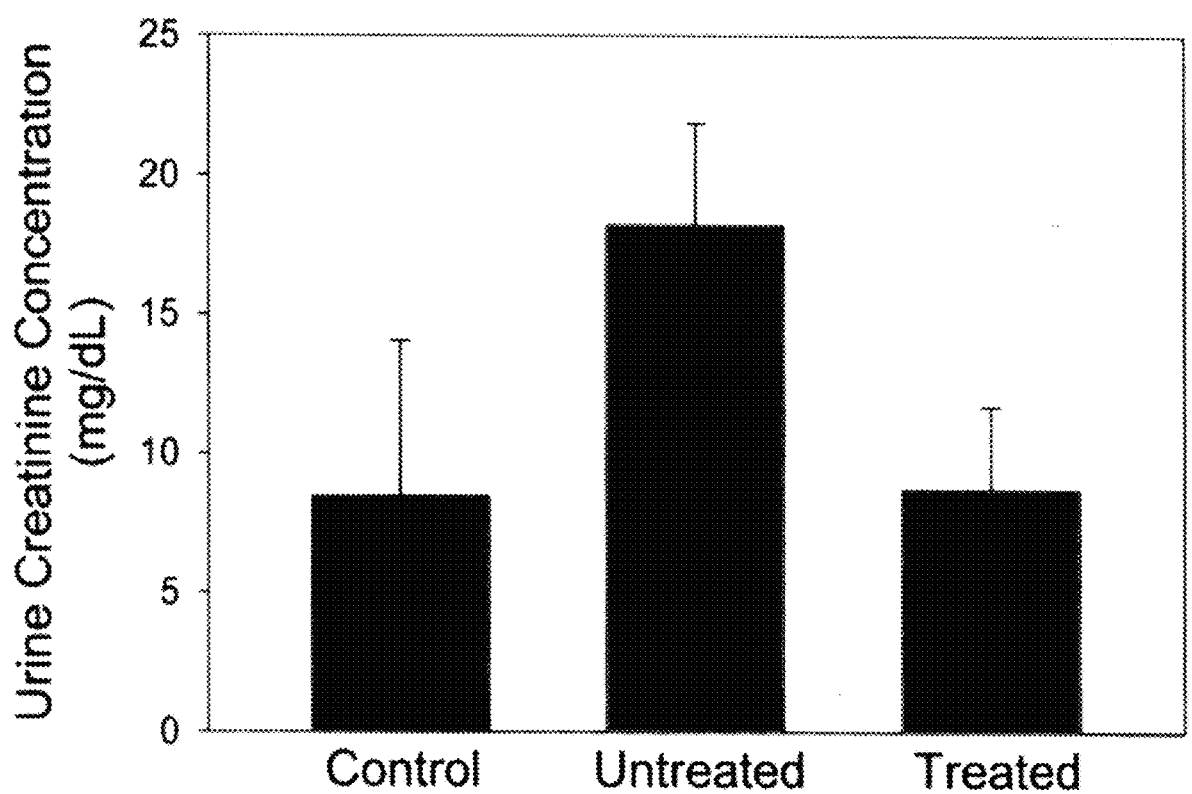
FIG. 5. Evidence that vaccine immunotherapy protects PKD1$^{v/v}$ kidney function. Urine samples were collected from D-6 control (n=4), untreated (n=4), and vaccine immunotherapy treated (n=7) mice and assayed using mouse creatinine assay kit (Crystal Chem, Catalog #80350). Experimental data show that urine creatinine concentrations for D-6 kidneys were 8.44±5.6, 18.2±3.7, and 8.7±3.2 mg/dL for control, untreated, and vaccine treated mice, respectively. The urine creatinine concentration was elevated only in untreated mice. These data further demonstrate that vaccine immunotherapy protects PKD kidney function.

Method-6: Detection of NKA activator antibodies prevented PKD complications. FIGS. 2-6 reveal NKA antibody activator-based immunotherapy protected kidney function and prevented kidney enlargement and failure. FIGS. 2-5 provide evidence to demonstrate that NKA antibody activator protected kidney function and prevented kidney enlargement and failure. FIG. 5 demonstrated that the NKA antibody activator-based immunotherapy protected kidney function by maintaining a normal creatinine concentration.

What is claimed is:

1. A method for inhibiting polycystic kidney disease (PKD) cysts growth in a subject comprising administering a therapeutically effective amount of an antibody that only specifically binds to SEQ ID NO: 5 of the α subunit of the (Na⁺+K⁺)-ATPase to a subject in need thereof, wherein the heavy chain variable domain of the antibody comprises the amino acid sequence of SEQ ID NO: 12 and the light chain variable domain comprises the amino acid sequence of SEQ ID NO: 13.

2. The method of claim 1, wherein the antibody is antibody SSA412 or a humanized or human versions thereof, or a fragment or derivative thereof, wherein the antibody is a polyclonal antibody or a monoclonal antibody, wherein the antibody is selected from the group consisting of IgG1, IgG2, IgG3, IgG4, IgM, IgA1, IgA2, IgD, and IgE, wherein the antibody fragment comprises one or more conservative amino acid substitutions.

3. The method of claim 1, wherein the antibody is in a pharmaceutical formulation comprising the antibody and a pharmaceutically acceptable carrier.

4. The method of claim 1, wherein the subject has or is at greater risk than the general population for a disease or condition selected from the group consisting of one or more of the following diseases and conditions: PKD, PKD-induced high blood pressure, abnormal renal architecture, renal insufficiency, loss of kidney function, chronic pain, growth of cysts in kidney and liver, hematuria, development of an aneurysm, pregnancy complications, heart valve abnormalities, heart disease, colon problems, kidney failure, and irreversible end-stage kidney disease.

5. A method for treating PKD complications in a subject comprising administering an effective amount of an antibody that only specifically binds to SEQ ID NO: 5 of the α subunit of the (Na⁺+K⁺)-ATPase to a subject in need thereof-, wherein the heavy chain variable domain of the antibody comprises the amino acid sequence of SEQ ID NO: 12 and the light chain variable domain comprises the amino acid sequence of SEQ ID NO: 13.

6. The method of claim 5, wherein the antibody is antibody SSA412 or a humanized or human versions thereof, or a fragment or derivative thereof, wherein the antibody is a polyclonal antibody or a monoclonal antibody, wherein the antibody is selected from the group consisting of IgG1, IgG2, IgG3, IgG4, IgM, IgA1, IgA2, IgD, and IgE, wherein the antibody fragment comprises one or more conservative amino acid substitutions.

7. The method of claim 5, wherein the antibody is in a pharmaceutical formulation comprising the antibody and a pharmaceutically acceptable carrier.

8. The method of claim 5, wherein the subject has or is at greater risk than the general population for a disease or condition selected from the group consisting of wherein the subject has or is at greater risk than the general population for a disease or condition selected from the group consisting of PKD, PKD-induced high blood pressure, abnormal renal architecture, renal insufficiency, loss of kidney function, chronic pain, growth of cysts in kidney and liver, hematuria, development of an aneurysm, pregnancy complications, heart valve abnormalities, heart disease, colon problems, kidney failure, and irreversible end-stage kidney disease.

* * * * *